United States Patent
Lim et al.

(10) Patent No.: US 10,857,250 B2
(45) Date of Patent: Dec. 8, 2020

(54) APPARATUS AND METHOD FOR GENERATING ACTIVATED STERILIZATION SOLUTION

(71) Applicant: CODESTERI INC, Seoul (KR)

(72) Inventors: Tae Ho Lim, Seoul (KR); Kimin Song, Seoul (KR); Jin Ha Jeong, Yongin-si (KR); Yeongtak Song, Seoul (KR); Yoonje Lee, Changwon-si (KR)

(73) Assignee: CODESTERI INC, Seoul (KR)

( * ) Notice: Subject to any disclaimer, the term of this patent is extended or adjusted under 35 U.S.C. 154(b) by 33 days.

(21) Appl. No.: 16/136,718

(22) Filed: Sep. 20, 2018

(65) Prior Publication Data
US 2019/0015537 A1   Jan. 17, 2019

Related U.S. Application Data

(63) Continuation of application No. PCT/KR2017/001271, filed on Feb. 6, 2017.

(30) Foreign Application Priority Data

Feb. 5, 2016  (KR) .......... 10-2016-0015249
Feb. 5, 2016  (KR) .......... 10-2016-0015251
Feb. 5, 2016  (KR) .......... 10-2016-0015253

(51) Int. Cl.
*A61L 2/14*   (2006.01)
*A61L 2/22*   (2006.01)
(Continued)

(52) U.S. Cl.
CPC .......... *A61L 2/14* (2013.01); *A61L 2/186* (2013.01); *A61L 2/202* (2013.01); *A61L 2/22* (2013.01);
(Continued)

(58) Field of Classification Search
CPC ..... A61L 2/10; A61L 2/14; A61L 2/18; A61L 2/183; A61L 2/186; A61L 2/202;
(Continued)

(56) References Cited

U.S. PATENT DOCUMENTS

| | | | | |
|---|---|---|---|---|
| 629,513 A | * | 7/1899 | Liebscher | .......... A47L 15/06 239/220 |
| 2008/0233002 A1 | | 9/2008 | Mizuno et al. | |
| 2017/0312376 A1 | * | 11/2017 | Bae | .......... A61L 2/14 |

FOREIGN PATENT DOCUMENTS

| | | |
|---|---|---|
| JP | 2001-309966 A | 11/2001 |
| JP | 2009-519799 A | 5/2009 |

(Continued)

OTHER PUBLICATIONS

English-language machine translation of KR20150126612 (Year: 2015).*

(Continued)

*Primary Examiner* — Timothy C Cleveland
(74) *Attorney, Agent, or Firm* — Sughrue Mion, PLLC

(57) ABSTRACT

An apparatus for generating an activated sterilization solution is disclosed. The apparatus may include a plasma treatment unit for performing plasma discharge treatment on a gas, and a sterilization solution treatment unit for changing a sterilization solution into a droplet or mist state. The gas treated by the plasma discharge treatment may be mixed with the sterilization solution in the droplet or mist state.

20 Claims, 13 Drawing Sheets

(51) Int. Cl.
  *A61L 9/14* (2006.01)
  *A61L 2/18* (2006.01)
  *A61L 2/20* (2006.01)
  *A61L 9/22* (2006.01)
  *A61L 2/10* (2006.01)
(52) U.S. Cl.
  CPC . *A61L 9/14* (2013.01); *A61L 2/10* (2013.01); *A61L 2/208* (2013.01); *A61L 9/22* (2013.01); *A61L 2202/121* (2013.01); *A61L 2202/122* (2013.01); *A61L 2202/14* (2013.01); *A61L 2202/24* (2013.01); *A61L 2209/11* (2013.01); *A61L 2209/14* (2013.01); *A61L 2209/211* (2013.01); *A61L 2209/212* (2013.01)
(58) Field of Classification Search
  CPC ... A61L 2/208; A61L 2/22; A61L 9/03; A61L 9/14; A61L 9/22; A61L 2202/121; A61L 2202/122; A61L 2202/14; A61L 2202/15; A61L 2202/24; A61L 2209/11; A61L 2209/211; A61L 2209/212
  See application file for complete search history.

(56) References Cited

FOREIGN PATENT DOCUMENTS

| KR | 10-1250748 B1 | 4/2013 |
| KR | 10-1534817 B1 | 7/2015 |
| KR | 10-2015-0126612 A | 11/2015 |
| KR | 10-2015-0133764 A | 11/2015 |
| WO | 2015/008784 A1 | 1/2015 |

OTHER PUBLICATIONS

International Search Report for PCT/KR2017/001271 dated May 12, 2017 [PCT/ISA/210].
Written Opinion for PCT/KR2017/001271 dated May 12, 2017 [PCT/ISA/237].
International Preliminary Report on Patentability for PCT/KR2017/001271 dated Aug. 7, 2018 [PCT/ISA/373].

* cited by examiner

APPARATUS AND METHOD FOR GENERATING ACTIVATED STERILIZATION SOLUTION

CROSS-REFERENCE TO RELATED APPLICATION

This application is a continuation of pending International Application No. PCT/KR2017/001271, which was filed on Feb. 6, 2017 and claims priority to Korean Patent Application Nos. 10-2016-0015249, 10-2016-0015251, and 10-2016-0015253, filed on Feb. 5, 2016, Feb. 5, 2016, and Feb. 5, 2016, in the Korean Intellectual Property Office, the disclosures of which are hereby incorporated by reference in their entireties.

BACKGROUND

1. Field

The present disclosure herein relates to an apparatus and a method for generating an activated sterilization solution, and more particularly, to an apparatus and a method which are capable of sufficiently activating a sterilization solution.

2. Description of the Related Art

Generally, there is a need to maintain pure sterilization states in hospitals, laboratories, good manufacturing practice (GMP) facilities, animal breeding facilities, biological safety facilities of biological safety level (BSL)-3, and internal laboratories and production rooms of aseptic preparation and manufacture facilities of medicines and food. Unlike cleaning or disinfection, the sterilization may mean that all kinds of living microorganisms are completely removed through physical and chemical actions. In other words, the sterilization may mean high-level treatment.

A method using hydrogen peroxide and plasma has been suggested as a sterilization method. Generally, an apparatus using hydrogen peroxide and plasma activates a sterilization solution by high jet pressure and applies a high voltage of 17,000V to 20,000V to perform plasma discharge treatment on the sterilization solution. The sterilization solution jetted by the high jet pressure may rapidly pass through an electric field in this method, and thus it may be difficult to sufficiently activate the sterilization solution of a mist state.

SUMMARY

The present disclosure may provide an apparatus and a method for generating an activated sterilization solution, which are capable of sufficiently activating a sterilization solution.

In an aspect, an apparatus for generating an activated sterilization solution may include a plasma treatment unit for performing plasma discharge treatment on a gas, and a sterilization solution treatment unit for changing a sterilization solution into a droplet or mist state. The gas treated by the plasma discharge treatment may be mixed with the sterilization solution in the droplet or mist state.

In an embodiment, the sterilization solution treatment unit may include a storage container, and a droplet or mist generator provided in the storage container and used to change the sterilization solution into the droplet or mist state. The droplet or mist generator may include a rotary brush, and a driving unit for rotating the rotary brush.

In an embodiment, the droplet or mist generator may further include a blocking part fixed on a rotation path of the rotary brush over the sterilization solution and used to collide with the rotary brush.

In an embodiment, the plasma treatment unit may include a supply line providing a flow path through which the gas flows, the supply line having an outlet from which the gas treated by the plasma discharge treatment is discharged, and a pair of electrodes opposite to each other with the flow path interposed therebetween. The sterilization solution treatment unit may supply the sterilization solution in the droplet or mist state toward the outlet or toward the flow path between the electrodes.

In an embodiment, hydrogen peroxide and a first additive may be contained in the sterilization solution, and the first additive may include at least one of sodium pyrophosphate, magnesium sulfate, sodium silicate, citric acid, or diethylenetriaminepentaacetic acid (DTPA).

In an embodiment, hydrogen peroxide and a second additive may be contained in the sterilization solution, and the second additive may include diethylenetriaminepentaacetic acid (DTPA).

In an embodiment, the apparatus may further include a sterilization solution supply unit for supplying the sterilization solution to the sterilization solution treatment unit, and an ultraviolet irradiating unit for irradiating ultraviolet light to the sterilization solution stored in the sterilization solution supply unit.

In an embodiment, the apparatus may further include an ultraviolet irradiating unit for irradiating ultraviolet light into the sterilization solution treatment unit.

In an embodiment, the gas may include air, and the sterilization solution in the droplet or mist state may be combined with ozone included in the air treated by the plasma discharge treatment such that an activation degree of the sterilization solution in the droplet or mist state is increased.

In an embodiment, the apparatus may further include a reactor providing a space in which the gas treated by the plasma discharge treatment is mixed with the sterilization solution in the droplet or mist state.

In an aspect, a method for generating an activated sterilization solution may include treating a gas by plasma discharge treatment, changing a sterilization solution into a droplet or mist state, and mixing the gas treated by the plasma discharge treatment with the sterilization solution in the droplet or mist state.

In an embodiment, the gas may include air. The sterilization solution in the droplet or mist state may be combined with ozone included in the air treated by the plasma discharge treatment such that an activation degree of the sterilization solution in the droplet or mist state is increased, in the mixing of the gas treated by the plasma discharge treatment with the sterilization solution in the droplet or mist state.

In an embodiment, the sterilization solution may include hydrogen peroxide and an additive, and the additive may include at least one of sodium pyrophosphate, magnesium sulfate, sodium silicate, or diethylenetriaminepentaacetic acid (DTPA).

In an embodiment, the method may further include irradiating ultraviolet light to the sterilization solution. The sterilization solution may be activated by the irradiating of the ultraviolet light.

In an aspect, an apparatus for generating an activated sterilization solution may include a storage container for storing a sterilization solution, a sterilization solution treatment unit for changing the sterilization solution into a droplet or mist state, a circulation flow path for circulating the sterilization solution in the droplet or mist state formed in the storage container to an outside of the storage container, a first plasma treatment unit provided on the circulation flow path and used to perform plasma discharge treatment on the sterilization solution in the droplet or mist state which circulates through the circulation flow path, a supply flow path for supplying the sterilization solution in the droplet or mist state, which is treated by the plasma discharge treatment, from the storage container into the atmosphere, and a valve for selectively opening or closing the circulation flow path and the supply flow path.

In an embodiment, the apparatus may further include a valve controller for controlling the valve, and the valve controller may control the valve to open the supply flow path when a concentration of the sterilization solution in the droplet or mist state which is treated by the plasma discharge treatment corresponds to a predetermined reference value in the storage container.

In an embodiment, the apparatus may further include a valve controller for controlling the valve, and the valve controller may control the valve to close the circulation flow path and to open the supply flow path when the sterilization solution in the droplet or mist state formed in the storage container circulates through the circulation flow path for a predetermined time.

In an embodiment, the apparatus may further include a valve controller for controlling the valve, and the valve controller may control the valve to open the supply flow path when a pressure or temperature in the storage container corresponds to a predetermined reference value.

In an embodiment, the apparatus may further include an ultraviolet irradiating unit for irradiating ultraviolet light into the storage container.

In an embodiment, the apparatus may further include an ultraviolet irradiating unit for irradiating ultraviolet light into the sterilization solution treatment unit.

In an embodiment, the apparatus may further include a second plasma treatment unit provided on the supply flow path and used to secondarily plasma-treat the sterilization solution in the droplet or mist state which is treated by the plasma discharge treatment and is supplied into the atmosphere.

BEST MODE FOR CARRYING THE INVENTIVE CONCEPTS

An apparatus for generating an activated sterilization solution according to an embodiment of the inventive concepts may include a plasma treatment unit for performing plasma discharge treatment on a gas, and a sterilization solution treatment unit for changing a sterilization solution into a droplet or mist state. The gas treated by the plasma discharge treatment may be mixed with the sterilization solution in the droplet or mist state.

DETAILED DESCRIPTION OF THE EMBODIMENTS

The inventive concepts will now be described more fully hereinafter with reference to the accompanying drawings, in which exemplary embodiments of the inventive concepts are shown. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts.

It will be understood that when an element such as a layer, region or substrate is referred to as being “on” another element, it can be directly on the other element or intervening elements may be present. In addition, in the drawings, the thicknesses of layers and regions are exaggerated for clarity.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concepts explained and illustrated herein include their complementary counterparts. As used herein, the term “and/or” includes any and all combinations of one or more of the associated listed items.

The terminology used herein is for the purpose of describing particular embodiments only and is not intended to limit the invention. As used herein, the singular terms “a”, “an” and “the” are intended to include the plural forms as well, unless the context clearly indicates otherwise. It will be further understood that the terms “comprises”, “comprising”, “includes”, “including”, “have”, “has” and/or “having” when used herein, specify the presence of stated features, integers, steps, operations, elements, and/or components, but do not preclude the presence or addition of one or more other features, integers, steps, operations, elements, components, and/or groups thereof. Furthermore, it will be understood that when an element is referred to as being “connected” or “coupled” to another element, it may be directly connected or coupled to the other element or intervening elements may be present.

In addition, in explanation of the present invention, the descriptions to the elements and functions of related arts may be omitted if they obscure the subjects of the inventive concepts.

An apparatus for generating an activated sterilization solution and a sterilization method using the same according to embodiments of the inventive concepts may activate a sterilization solution. The sterilization solution may be provided in various kinds. In the present embodiments, a sterilization solution in which a small amount of hydrogen peroxide is contained in water will be described as an example. In detail, hydrogen peroxide is contained at a low concentration of 7.5% or less in the sterilization solution. Hydrogen peroxide may be contained at a concentration of 7.5% or 3.0% in the sterilization solution.

In addition, a first additive and a second additive may be contained in the sterilization solution.

The first additive may be provided to remove metal ions included in the sterilization solution. Decomposition of hydrogen peroxide may be accelerated by a small amount of metal ions (Mn, Fe, Cu, Pb, Ag, and/or Pt) included in the sterilization solution. Therefore, hydrogen peroxide may be stabilized by removing these metal ions. The first additive may include at least one of sodium pyrophosphate, magnesium sulfate, sodium silicate, citric acid, or diethylenetriaminepentaacetic acid (DTPA).

The second additive may improve a disinfection or sterilization effect by combination with hydrogen peroxide. In an embodiment, the second additive may include DTPA. DTPA may react with hydrogen peroxide to generate peracetic acid. The peracetic acid may have an excellent effect of sterilizing microorganisms, may not form chlorine disinfection by-products, and may perform environmentally friendly decomposition. In addition, the DTPA may have a long shelf life of 12 months to 18 months and may minimize dependence on pH and temperature. Furthermore, handling and storage of the DTPA may be stable and simple.

Hereinafter, the apparatus for generating an activated sterilization solution according to some embodiments of the inventive concepts will be described with reference to the accompanying drawings.

Figure 1:
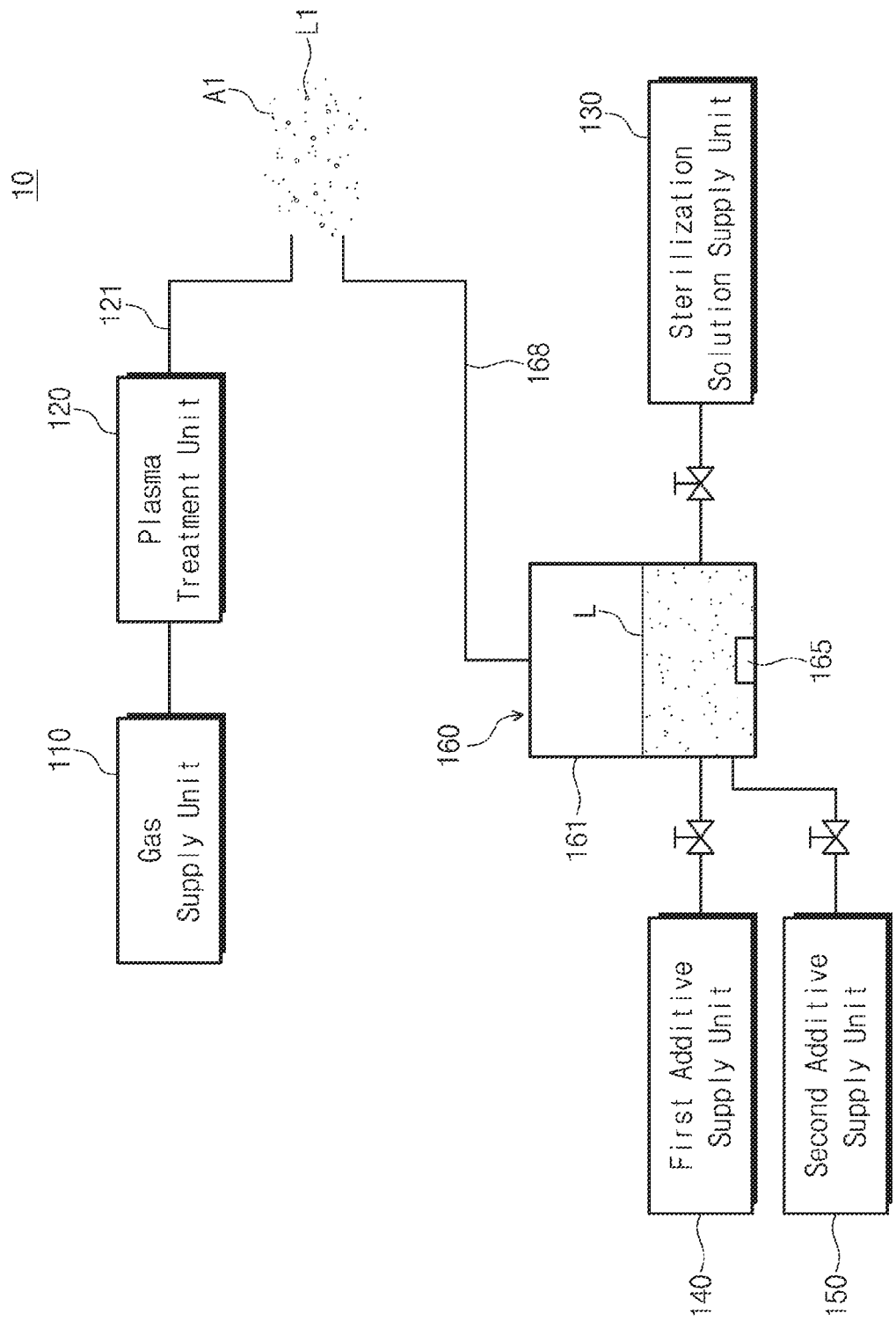
FIG. 1 is a view illustrating an apparatus for generating an activated sterilization solution, according to an embodiment of the inventive concepts.

FIG. 1 is a view illustrating an apparatus for generating an activated sterilization solution, according to an embodiment of the inventive concepts.

Referring to FIG. 1, an apparatus 10 for generating an activated sterilization solution may include a gas supply unit 110, a plasma treatment unit 120, a sterilization solution supply unit 130, a first additive supply unit 140, a second additive supply unit 150, and a sterilization solution treatment unit 160.

The gas supply unit 110 may supply a gas to the plasma treatment unit 120. The gas may include at least one of air, nitrogen, or helium. In the present embodiment, the air will be described as an example of the gas.

The gas supply unit 110 may supply external air to the plasma treatment unit 120. In an embodiment, the gas supply unit 110 may include a fan or a pump.

The plasma treatment unit 120 may perform plasma discharge treatment on the air. The air treated by the plasma discharge treatment may include ozone, nitrogen oxide, hydroxide base, carbon dioxide, and/or carbon monoxide. Ozone, nitrogen oxide, hydroxide base, etc., may be more unstable in the treated air than in the atmosphere and may be in an activated radical state.

The sterilization solution supply unit 130 may supply the sterilization solution to the sterilization solution treatment unit 160.

The first additive supply unit 140 may supply the first additive to the sterilization solution treatment unit 160, and the second additive supply unit 150 may supply the second additive to the sterilization solution treatment unit 160.

In the present embodiment, the first additive is supplied to the sterilization solution treatment unit 160 through the first additive supply unit 140, and the second additive is supplied to the sterilization solution treatment unit 160 through the second additive supply unit 150. Alternatively, the first additive and the second additive may be contained previously in the sterilization solution stored in the sterilization solution supply unit 130.

The sterilization solution treatment unit 160 may change the sterilization solution into a droplet or mist state. The sterilization solution treatment unit 160 may include a storage container 161 and a droplet or mist generator 165.

The sterilization solution L may be stored in the storage container 161.

The droplet or mist generator 165 may change the sterilization solution L stored in the storage container 161 into the droplet or mist state.

In an embodiment, the droplet or mist generator 165 may include an ultrasonic vibrator, and the sterilization solution L may be changed into the droplet or mist state by vibration of the ultrasonic vibrator.

In another embodiment, the droplet or mist generator 165 may include a bubbler. The bubbler may generate bubbles to change the sterilization solution L into the droplet or mist state.

In still another embodiment, the droplet or mist generator 165 may apply heat to the storage container 161 to boil the sterilization solution L, and thus the sterilization solution L may be changed into the droplet or mist state.

In yet another embodiment, the droplet or mist generator 165 may include a heating plate which is immersed in the sterilization solution L in the storage container 161. The heating plate may be a device emitting heat by a current applied thereto, and the current may be periodically and repeatedly applied to the heating plate. The heating plate may be heated to a high temperature in a short time by the current applied thereto, and bubbles may be formed on the heating plate in this process. The bubbles may change the sterilization solution L into the droplet or mist state.

Figure 2:
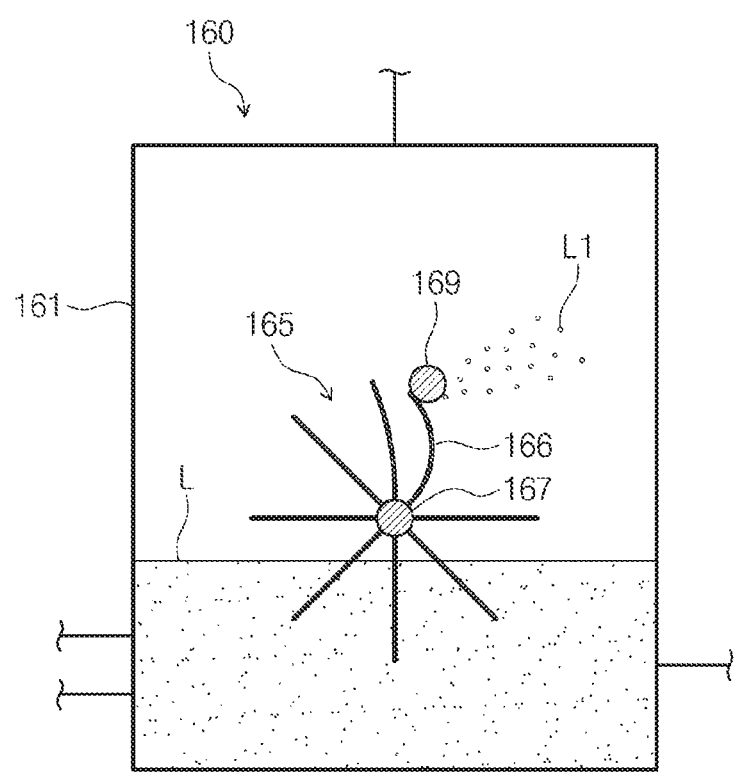
FIG. 2 is a view illustrating a droplet or mist generator according to an embodiment of the inventive concepts.

FIG. 2 is a view illustrating a droplet or mist generator according to an embodiment of the inventive concepts.

Referring to FIG. 2, the droplet or mist generator 165 may include a rotary brush 166, a driving unit (not shown), and a blocking part 169.

The rotary brush 166 may be provided along a circumference of a rotary shaft 167. A portion of the rotary brush 166 may be immersed in the sterilization solution L, and the other portion of the rotary brush 166 may be provided outside the sterilization solution L. The rotary brush 166 may be rotated together with the rotary shaft 167 by the driving unit. In the rotation process, the rotary brush 166 may be repeatedly immersed in the sterilization solution L.

The blocking part 169 may be fixed on a rotation path of the rotary brush 166 over the sterilization solution L. An end portion of the rotary brush 166 may collide with the blocking part 169 in the rotation process. The sterilization solution L in the rotary brush 166 may be dispersed in the droplet or mist state L1 in the storage container 161 by collision force of the rotary brush 166 and the blocking part 169.

Figure 3:
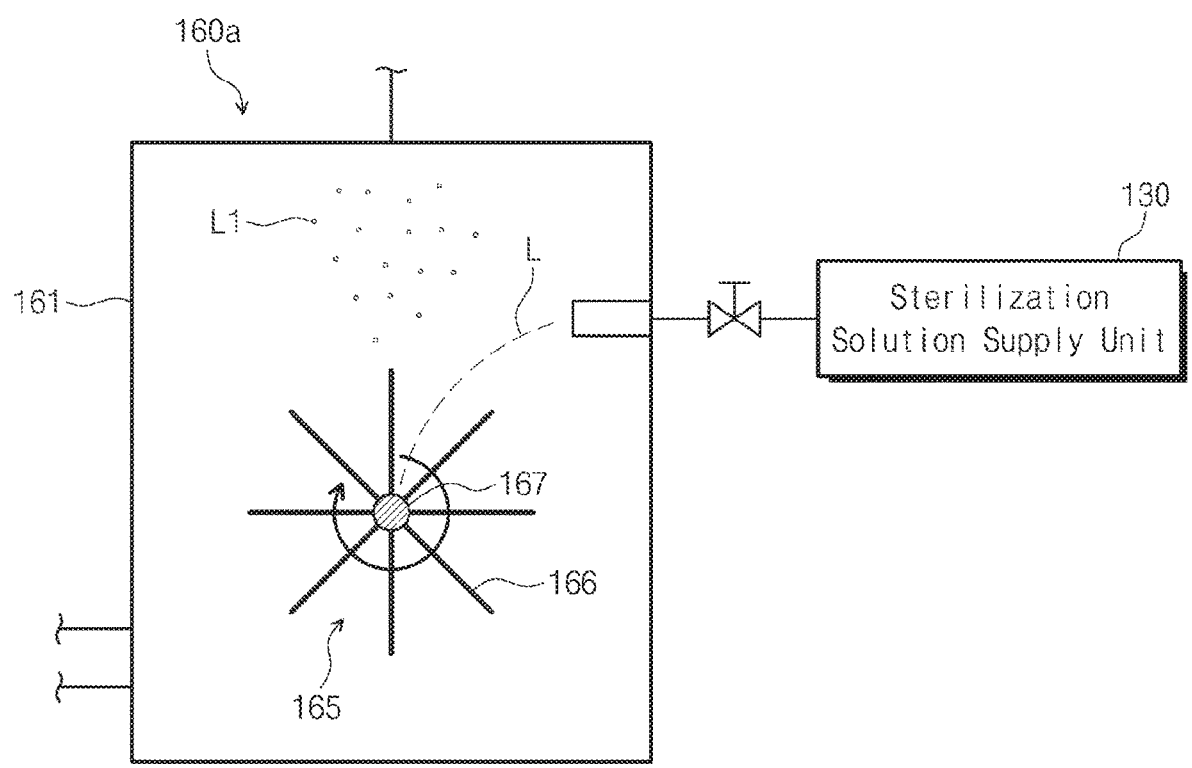
FIG. 3 is a view illustrating a sterilization solution treatment unit according to an embodiment of the inventive concepts.

FIG. 3 is a view illustrating a sterilization solution treatment unit according to an embodiment of the inventive concepts.

Referring to FIG. 3, a sterilization solution treatment unit 160a may include a storage container 161 and a droplet or mist generator 165.

The storage container 161 may provide a space in which droplets or mist L1 are/is generated from the sterilization solution L.

The droplet or mist generator 165 may generate droplets or mist L1 from the sterilization solution L supplied into the storage container 161. The droplet or mist generator 165 may include a rotary brush 166 and a driving unit (not shown).

The rotary brush 166 may be located in the storage container 161 and may be provided along a circumference of a rotary shaft 167. The rotary brush 166 may be rotated together with the rotary shaft 167 by the driving unit.

The sterilization solution L may be supplied from the sterilization solution supply unit 130 into the storage container 161, and the rotary brush 166 may be rotated by the driving unit and may collide with the sterilization solution L. The sterilization solution L may be dispersed in the droplet or mist state L1 by collision force with the rotary brush 166.

Referring again to FIG. 1, the air A1 treated by the plasma discharge treatment may be discharged from a supply line 121 included in the plasma treatment unit 120, and the sterilization solution L1 in the droplet or mist state may be discharged from a supply line 168 connected to the sterilization solution treatment unit 160. The air A1 discharged from the supply line 121 may be mixed with the sterilization solution L1 in the droplet or mist state, which is discharged from the supply line 168. In an embodiment, the air A1 treated by the plasma discharge treatment may be mixed with the sterilization solution L1 in the droplet or mist state in the atmosphere. The sterilization solution L1 in the droplet or mist state may be combined with radicals included in the air A1 treated by the plasma discharge treatment, and thus an activation degree of the sterilization solution L1 may be increased. In an embodiment, the sterilization solution L1 in the droplet or mist state may be mainly combined with ozone included in the air A1 treated by the plasma discharge treatment, and thus the activation degree of the sterilization solution L1 may be increased. The increase in the activation degree may affect improvement of sterilizing power. A mixture gas in which the air A1 treated by the plasma discharge treatment is mixed with the sterilization solution L1 in the droplet or mist state may be diffused in the atmosphere to sterilize a pollutant.

Figure 4:
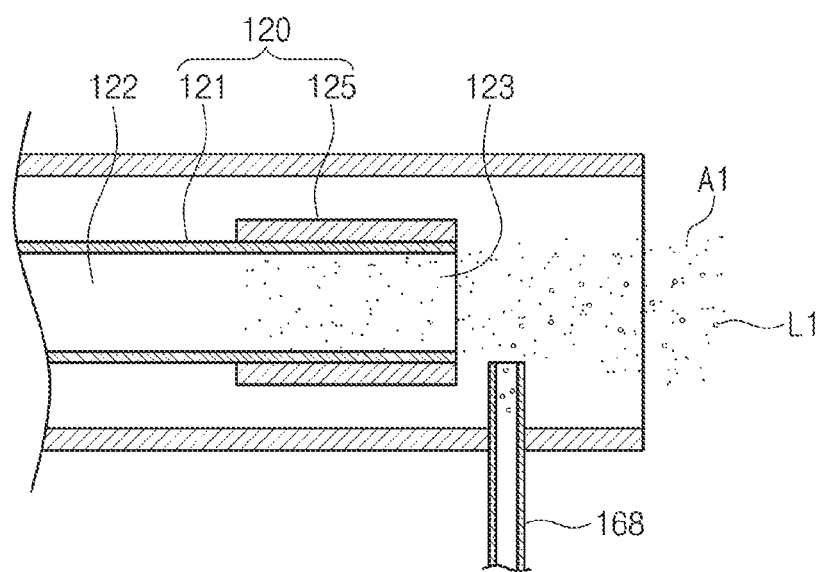
FIG. 4 is a view illustrating an example of the apparatus for generating an activated sterilization solution in FIG. 1.
Figure 5:
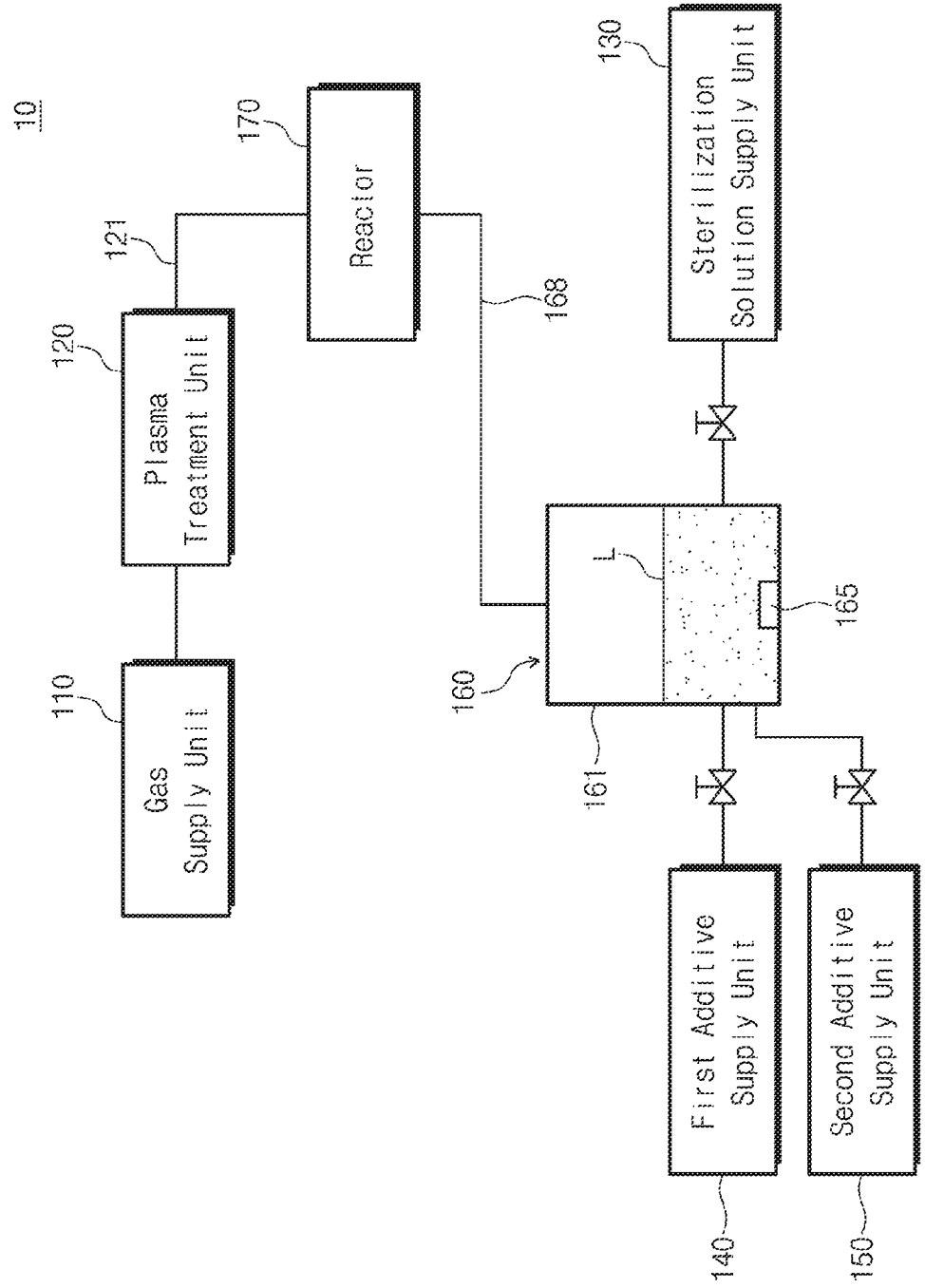
FIGS. 5 to 16 are views illustrating apparatuses for generating an activated sterilization solution, according to some embodiments of the inventive concepts.
Figure 6:
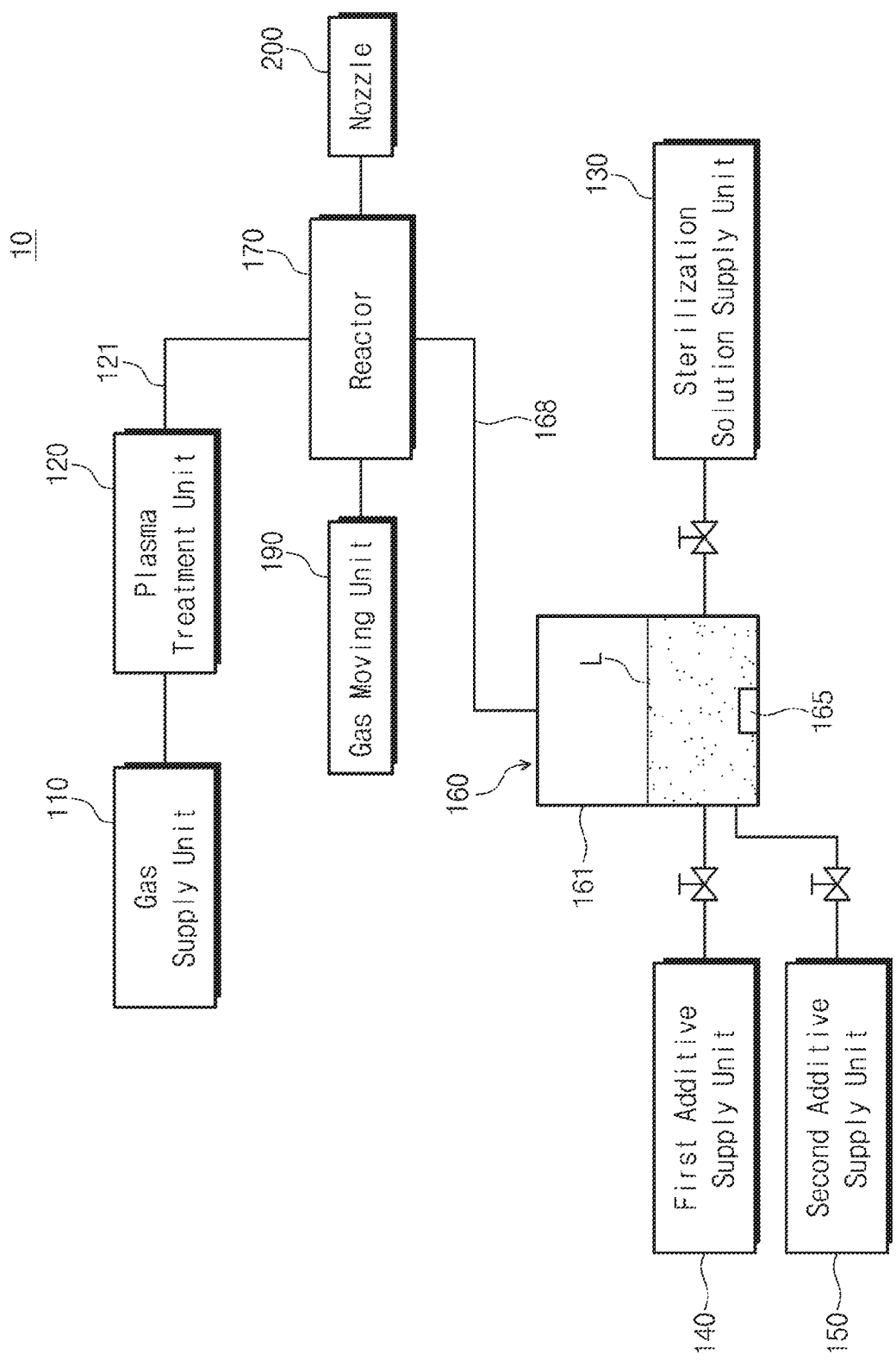
Figure 7:
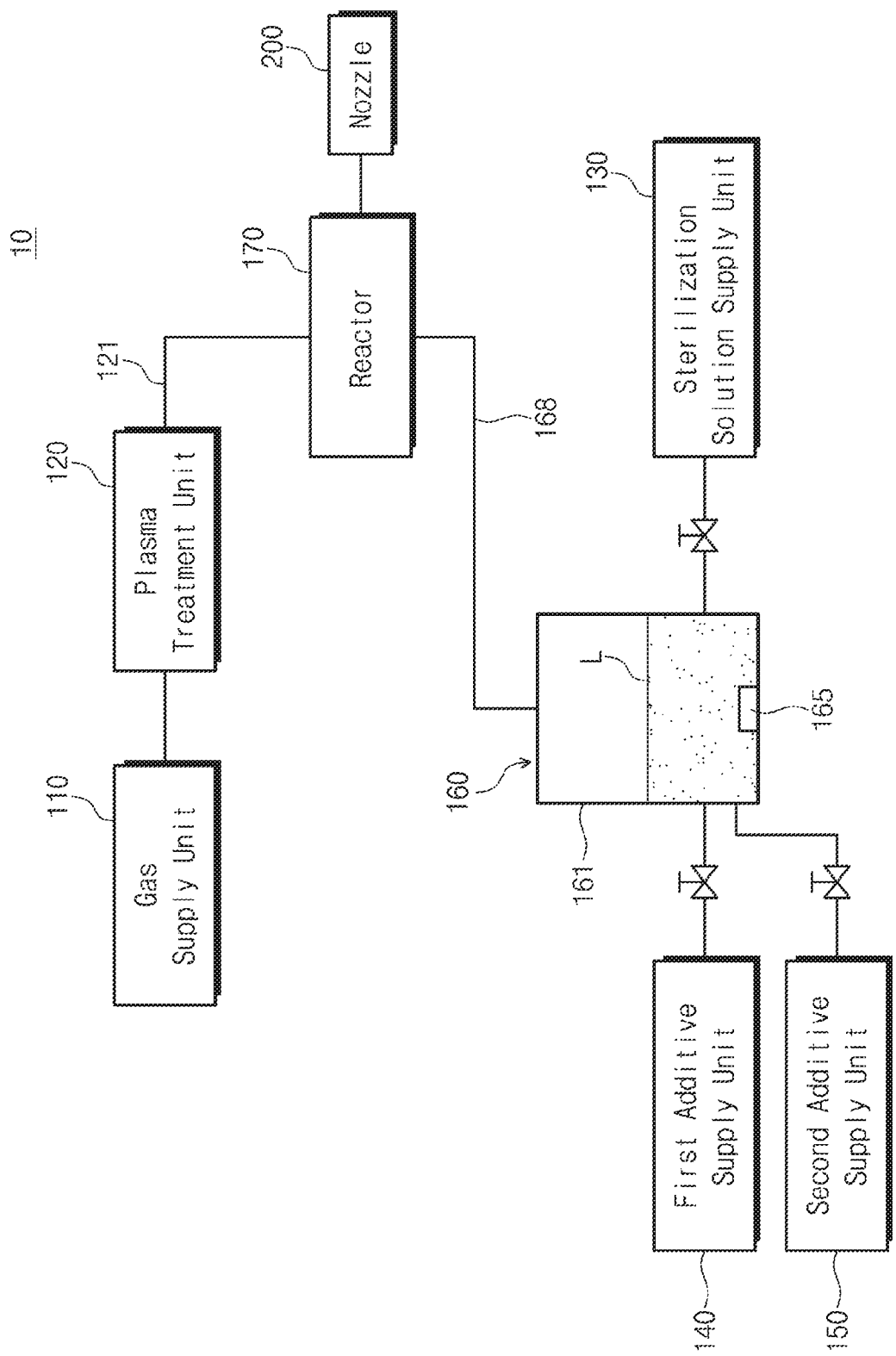
Figure 8:
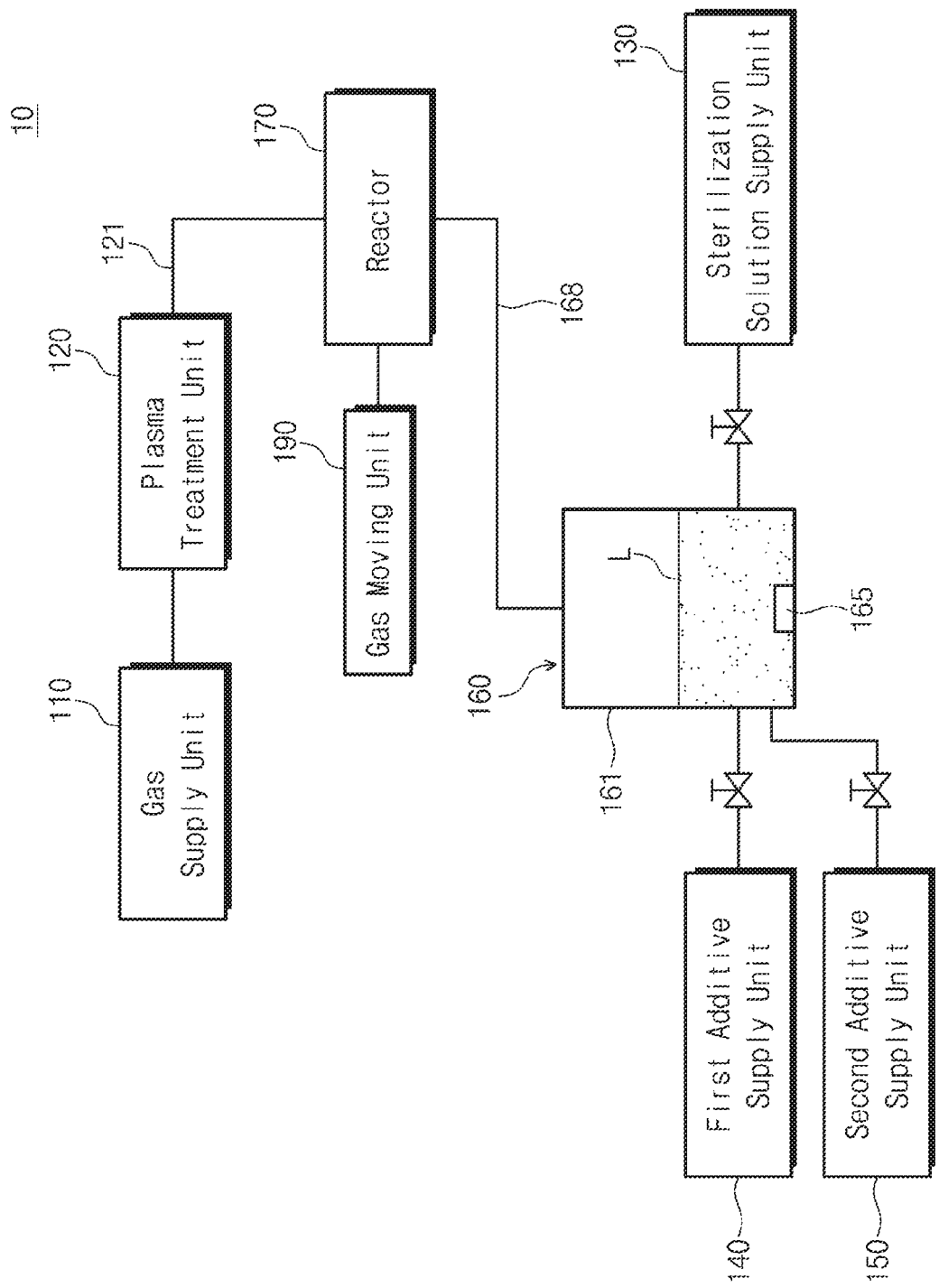
Figure 9:
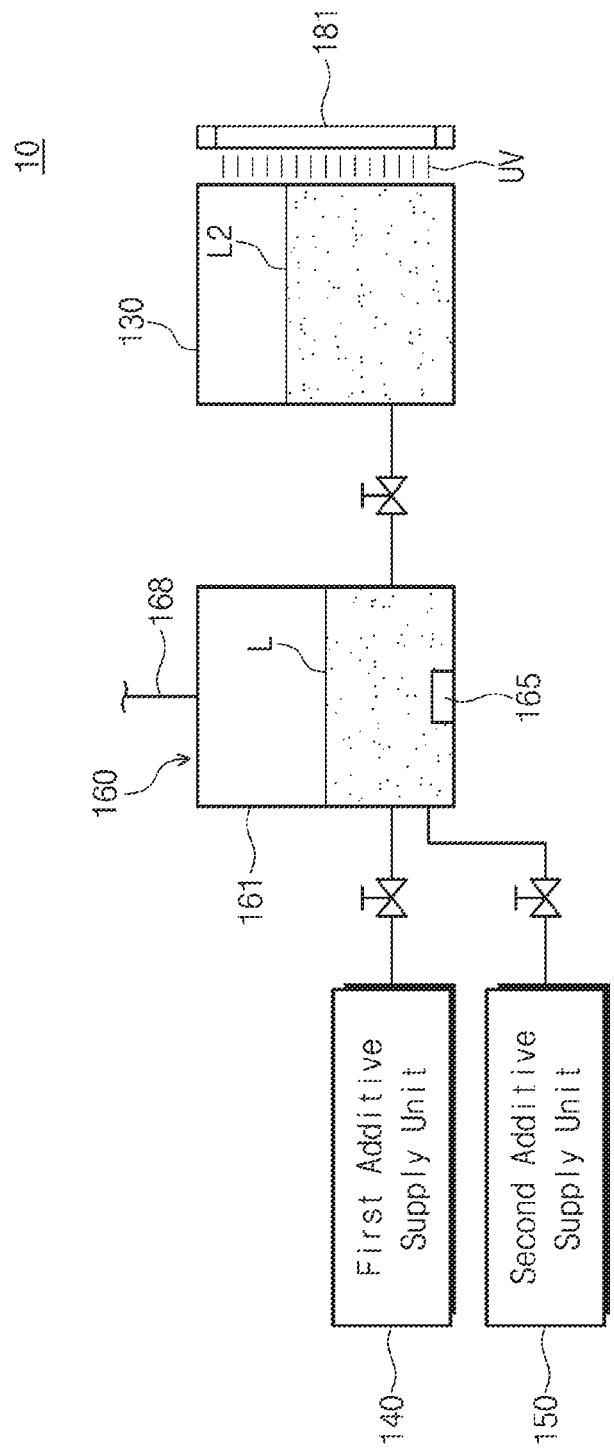

FIG. 4 is a view illustrating an example of the apparatus for generating an activated sterilization solution in FIG. 1.

Referring to FIGS. 1 and 4, the plasma treatment unit 120 may include the supply line 121 and an electrode 125.

The supply line 121 may provide a flow path 122 into which the air is supplied. The supply line 121 may be formed of a dielectric material. An outlet 123 from which the air treated by the plasma discharge treatment is discharged may be provided at an end of the supply line 121.

The electrode 125 may include a pair of electrodes 125 opposite to each other with the flow path 122 interposed therebetween, and a voltage may be applied to the electrodes 125 by an external power source. An electric field may be formed in a space between the electrodes 125 (i.e., in the flow path 122 of the supply line 121) by the applied voltage, and thus the plasma discharge treatment may be performed on the air by the electric field to convert the air into radicals.

Figure 10:
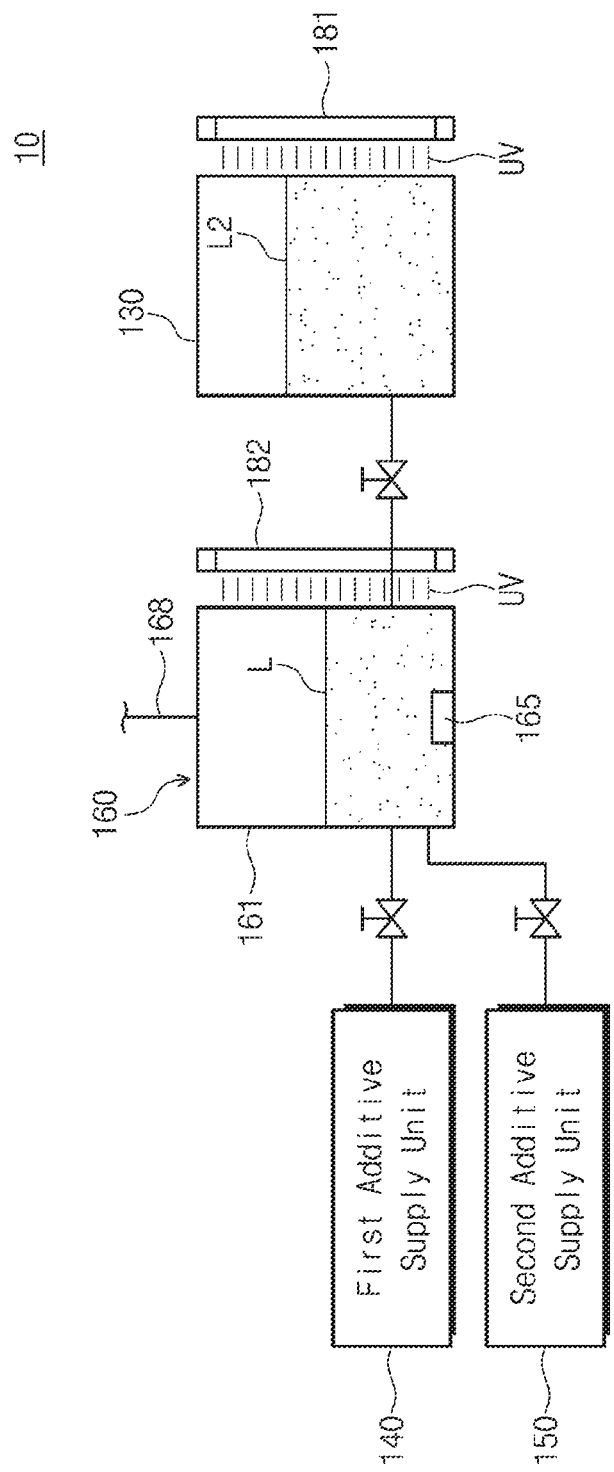

The sterilization solution L1 in the droplet or mist state which is supplied from the storage container 161 may be supplied through the supply line 168. An end of the supply line 168 may be located in front of the outlet 123, and the sterilization solution L1 in the droplet or mist state may be supplied toward the air A1 treated by the plasma discharge treatment which is discharged from the outlet 123. The sterilization solution L1 in the droplet or mist state may be mixed and combined with the air A1 immediately after being treated by the plasma discharge treatment, and thus the activation degree of the sterilization solution L1 may be increased. The radicals may have a short half-life in the atmosphere, not in a vacuum state. Thus, the radicals may lose energy in a short time and may return to a stable state. However, according to the embodiment of the inventive concepts, the sterilization solution L1 in the droplet or mist state may be supplied to the air A1 immediately after the plasma discharge treatment, and thus the sterilization solution L1 in the droplet or mist state may be activated using high energy of the air A1 treated by the plasma discharge treatment.

FIG. 5 is a view illustrating an apparatus for generating an activated sterilization solution, according to another embodiment of the inventive concepts.

Referring to FIG. 5, an apparatus 10 for generating an activated sterilization solution may further include a reactor 170. The reactor 170 may be connected to the supply line 121 for supplying the air treated by the plasma discharge treatment and the supply line 168 for supplying the sterilization solution in the droplet or mist state. The reactor 170 may provide a space in which the air treated by the plasma discharge treatment is mixed with the sterilization solution in the droplet or mist state. The air treated by the plasma discharge treatment and the sterilization solution in the droplet or mist state may be mixed with each other in the reactor 170 and then may be discharged from the reactor 170 to the outside.

FIG. 6 is a view illustrating an apparatus for generating an activated sterilization solution, according to still another embodiment of the inventive concepts.

Referring to FIG. 6, an apparatus 10 for generating an activated sterilization solution may further include a gas moving unit 190 and a nozzle 200. The gas moving unit 190 may be connected to the reactor 170 and may move a mixture gas of the air treated by the plasma discharge treatment and the sterilization solution in the droplet or mist state in the reactor 170 to the nozzle 200. In an embodiment, the gas moving unit 190 may include a fan or a pump.

The nozzle 200 may be connected to the reactor 170 and may jet the mixture gas of the air treated by the plasma discharge treatment and the sterilization solution in the droplet or mist state in the reactor 170 to the outside.

FIGS. 7 and 8 are views illustrating apparatuses for generating an activated sterilization solution, according to yet other embodiments of the inventive concepts.

Referring to FIGS. 7 and 8, unlike the embodiment of FIG. 6, one of the gas moving unit 190 and the nozzle 200 may be provided in the apparatus 10 to supply the mixture gas of the air treated by the plasma discharge treatment and the sterilization solution in the droplet or mist state in the reactor 170 to the outside.

FIG. 9 is a view illustrating a portion of an apparatus for generating an activated sterilization solution, according to still yet another embodiment of the inventive concepts.

Referring to FIG. 9, an apparatus 10 for generating an activated sterilization solution may further include an ultraviolet irradiating unit 181. The ultraviolet irradiating unit 181 may irradiate ultraviolet light UV to the sterilization solution L2 stored in the sterilization solution supply unit 130. Hydrogen peroxide may be more unstable than water and may be activated by the irradiation of the ultraviolet light UV. In detail, hydrogen peroxide may be activated to $H_2O_2$, $H_2O$, and/or $OH^-$ by the irradiation of the ultraviolet light UV.

The sterilization solution L2 activated by the ultraviolet light UV may be supplied into the storage container 161 and may be secondarily changed into a droplet or mist state by the droplet or mist generator 165. In addition, the sterilization solution in the droplet or mist state may be mixed with the air treated by the plasma discharge treatment so as to be additionally activated. The increase in the activation of the sterilization solution may improve sterilizing power thereof.

FIG. 10 is a view illustrating a portion of an apparatus for generating an activated sterilization solution, according to still yet another embodiment of the inventive concepts.

Referring to FIG. 10, an apparatus 10 for generating an activated sterilization solution may further include a first ultraviolet irradiating unit 181 and a second ultraviolet irradiating unit 182. The first ultraviolet irradiating unit 181 may irradiate ultraviolet light UV to the sterilization solution L2 stored in the sterilization solution supply unit 130, and the second ultraviolet irradiating unit 182 may irradiate ultraviolet light UV to the sterilization solution L and the sterilization solution changed into the droplet or mist state in the sterilization solution treatment unit 160. Since the ultraviolet lights UV are irradiated to the sterilization solution L2 in the sterilization solution supply unit 130 and the sterilization solution L and the sterilization solution changed into the droplet or mist state in the sterilization solution treatment unit 160, the activation of the sterilization solution may be more increased.

Figure 11:
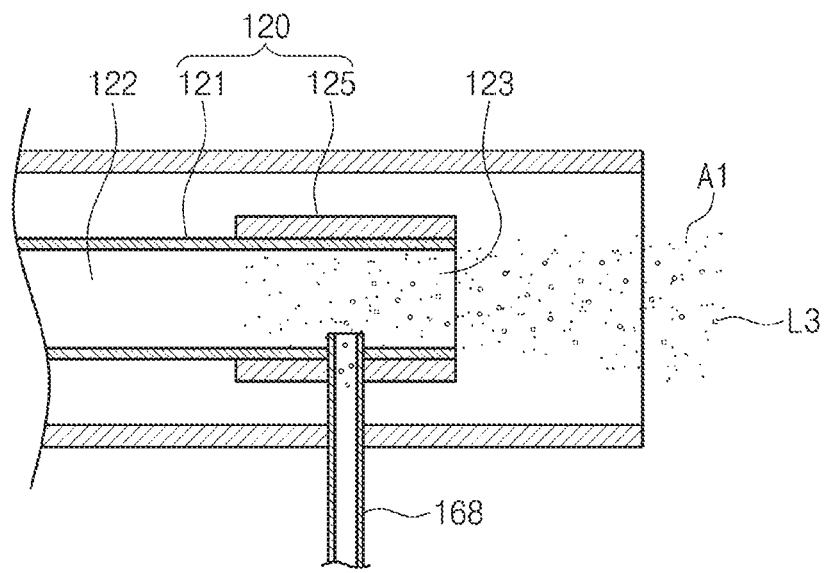

FIG. 11 is a view illustrating a portion of an apparatus for generating an activated sterilization solution, according to still yet another embodiment of the inventive concepts.

Referring to FIG. 11, the supply line 168 may supply a sterilization solution L3 in a droplet or mist state into the flow path 122 of the supply line 121 between the electrodes 125. The sterilization solution L3 in the droplet or mist state may be treated together with the air A1 supplied through the supply line 121 by the plasma discharge treatment. The electric field formed between the electrodes 125 by the voltage applied to the electrodes 125 may activate the air A1 and the sterilization solution L3 in the droplet or mist state to a radical state.

Figure 12:
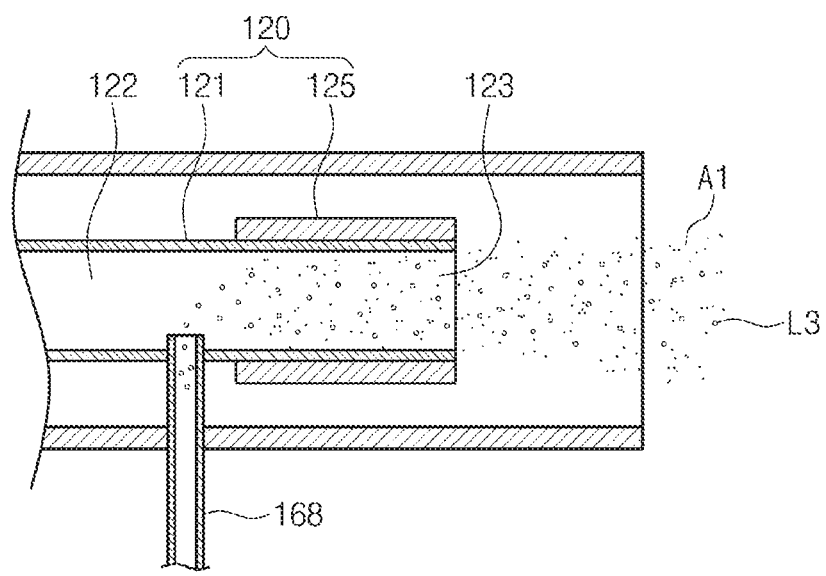

FIG. 12 is a view illustrating a portion of an apparatus for generating an activated sterilization solution, according to still yet another embodiment of the inventive concepts.

Referring to FIG. 12, the supply line 168 may supply the sterilization solution L3 in the droplet or mist state into the flow path 122 of the supply line 121 located in front of the electrode 125. The sterilization solution L3 in the droplet or mist state may be mixed with the air A1, and the mixture gas thereof may flow through the space between the electrodes 125. In addition, the mixture gas may be plasma-discharge-treated by the electric field formed in the space between the electrodes 125 by the voltage applied to the electrodes 125.

Figure 13:
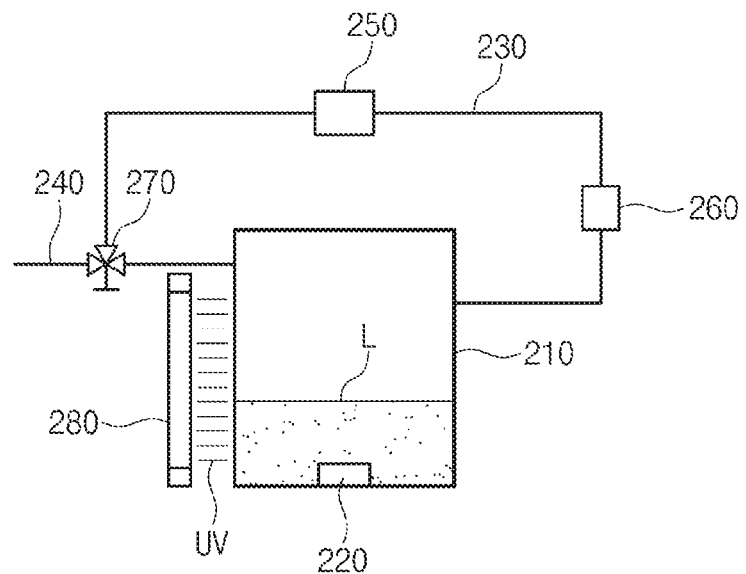

FIG. 13 is a view illustrating an apparatus for generating an activated sterilization solution, according to still yet another embodiment of the inventive concepts.

Referring to FIG. 13, an apparatus 20 for generating an activated sterilization solution may include a storage container 210, a sterilization solution treatment unit 220, a circulation flow path 230, a supply flow path 240, a circulation driving unit 250, a first plasma treatment unit 260, and an ultraviolet irradiating unit 280.

The storage container 210 may store a sterilization solution L.

The sterilization solution treatment unit 220 may be provided in the storage container 210 and may change the sterilization solution L into a droplet or mist state. The sterilization solution treatment unit 220 may be the same as the droplet or mist generator described with reference to FIGS. 1 to 3.

The circulation flow path 230 may circulate the sterilization solution in the droplet or mist state formed in the storage container 210 to the outside of the storage container 210.

The supply flow path 240 may supply a plasma-discharge-treated sterilization solution remaining in the storage container 210 to the outside of the storage container 210. The supply flow path 240 may supply the plasma-discharge-treated sterilization solution into the atmosphere.

A valve 270 may control the sterilization solution in the droplet or mist state in such a way that it is supplied to the circulation flow path 230 or the supply flow path 240. Even though not shown in the drawings, the valve 270 may be automatically controlled by a valve controller.

The circulation driving unit 250 and the first plasma treatment unit 260 may be provided on the circulation flow path 230. The circulation driving unit 250 may provide force or power to the sterilization solution in the droplet or mist state to allow it to circulate through the circulation flow path 250. In an embodiment, the circulation driving unit 250 may include a fan or a pump.

The first plasma treatment unit 260 may include two electrodes which are opposite to each other with the circulation flow path 230 interposed therebetween. The first plasma treatment unit 260 may form an electric field in the circulation flow path 230 by a voltage applied thereto. Plasma discharge treatment may be performed on the sterilization solution in the droplet or mist state by the electric field to form a radical state of the sterilization solution.

While the sterilization solution in the droplet or mist state repeatedly circulates through the circulation flow path 230, the amount of the radicals of the plasma-discharge-treated sterilization solution may be increased in the storage container 210. Temperature and pressure in the storage container 210 may increase as the amount of the radicals of the plasma-discharge-treated sterilization solution increases.

The ultraviolet irradiating unit 280 may irradiate ultraviolet light UV to the sterilization solution L, the sterilization solution in the droplet or mist state, and the plasma-discharge-treated sterilization solution in the storage container 210. Activation of the sterilization solution L, the sterilization solution in the droplet or mist state, and the plasma-discharge-treated sterilization solution in the storage container 210 may be more increased by the irradiation of the ultraviolet light UV.

When a concentration of the radicals of the sterilization solution in the storage container 210 is increased to a predetermined reference value or more, the valve controller may control the valve 270 to block the circulation flow path 230 and to open the supply flow path 240. Thus, the radicals of the sterilization solution may be released and diffused into the atmosphere through the supply flow path 240 so as to be supplied to an object to be sterilized.

On the other hand, the valve controller may control the valve 270 on the basis of a process time. In more detail, a time for which the sterilization solution in the droplet or mist state circulates through the circulation flow path 230 may be set, and the valve controller may control the valve 270 to open the supply flow path 240 when an elapsed time corresponds to the set time.

In a certain embodiment, when the pressure or temperature in the storage container 210 is increased to a predetermined reference value or more, the valve controller may control the valve 270 to block the circulation flow path 230 and to open the supply flow path 240.

Figure 14:
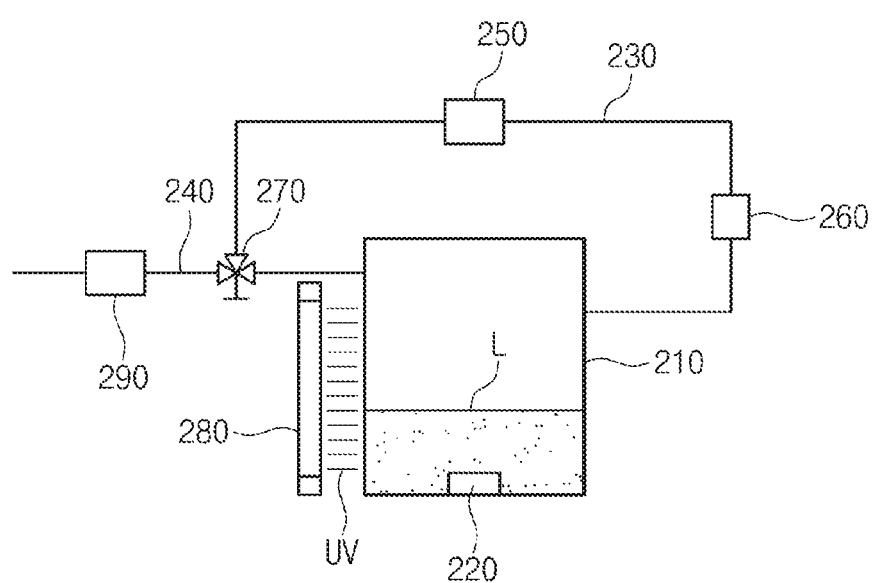

FIG. 14 is a view illustrating an apparatus for generating an activated sterilization solution, according to still yet another embodiment of the inventive concepts.

Referring to FIG. 14, an apparatus 20 for generating an activated sterilization solution may further include a second plasma treatment unit 290. The second plasma treatment unit 290 may be provided on the supply flow path 240 and may secondarily treat the plasma-discharge-treated sterilization solution, supplied through the supply flow path 240, by plasma discharge treatment. Since the second plasma treatment unit 290 secondarily plasma-discharge-treats the plasma-discharge-treated sterilization solution immediately before being supplied to an object to be sterilized, the activation of the plasma-discharge-treated sterilization solution may be more increased.

Figure 15:
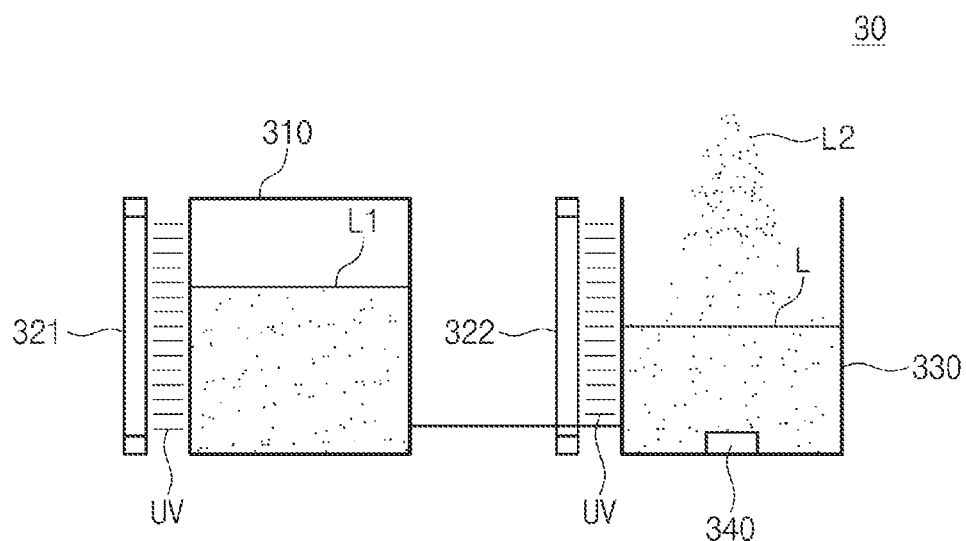

FIG. 15 is a view illustrating an apparatus for generating an activated sterilization solution, according to still yet another embodiment of the inventive concepts.

Referring to FIG. 15, an apparatus 30 for generating an activated sterilization solution may include a sterilization solution supply unit 310, a first ultraviolet irradiating unit 321, a second ultraviolet irradiating unit 322, a storage container 330, and a sterilization solution treatment unit 340.

The sterilization solution supply unit 310 may store a sterilization solution L.

The first ultraviolet irradiating unit 321 may irradiate ultraviolet light UV to the sterilization solution L stored in the sterilization solution supply unit 310. Hydrogen peroxide may be more unstable than water and may be activated by the irradiation of the ultraviolet light UV. In detail, hydrogen peroxide may be activated to $H_2O_2$, $H_2O$, and/or $OH^-$ by the irradiation of the ultraviolet light UV.

The storage container 330 may store the sterilization solution L1 which is activated by the ultraviolet light UV and is supplied from the sterilization solution supply unit 310.

The sterilization solution treatment unit 340 may change the sterilization solution L1 stored in the storage container 330 into a droplet or mist state. The sterilization solution treatment unit 340 may be the same as the droplet or mist generator described with reference to FIGS. 1 to 3.

The sterilization solution L2 in the droplet or mist state may be diffused to the outside in the form of smoke or fog and may sterilize a pollutant.

The second ultraviolet irradiating unit 322 may irradiate ultraviolet light UV to the sterilization solution L1 and the sterilization solution L2 in the droplet or mist state in the storage container 330. Since the ultraviolet lights UV are irradiated to the sterilization solution L in the sterilization solution supply unit 310 and the sterilization solution L1 and the sterilization solution L2 in the droplet or mist state in the storage container 330, the activation of the sterilization solution may be more increased.

Figure 16:
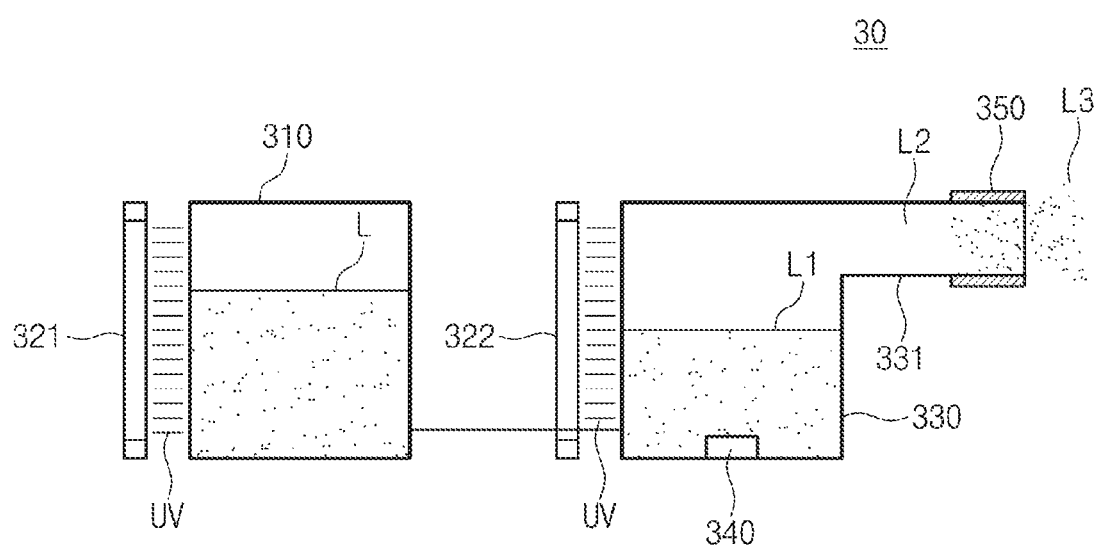

FIG. 16 is a view illustrating an apparatus for generating an activated sterilization solution, according to still yet another embodiment of the inventive concepts.

Referring to FIG. 16, an apparatus 30 for generating an activated sterilization solution may further include a plasma treatment unit 350 in addition to the apparatus of FIG. 15.

The plasma treatment unit 350 may be provided at an outlet port 331 from which the sterilization solution L2 in the droplet or mist state in the storage container 330 is discharged. The plasma treatment unit 350 may include two electrodes which are opposite to each other with the outlet port 331 interposed therebetween. The plasma treatment unit 350 may form an electric field in the outlet port 331 by a voltage applied thereto. Plasma discharge treatment may be performed on the sterilization solution L2 in the droplet or mist state by the electric field to form a radical state L3.

According to the present embodiment, the sterilization solution L may be primarily activated by the irradiation of the ultraviolet light UV and then may be secondarily activated by the sterilization solution treatment unit 340 and the irradiation of the ultraviolet light UV. In addition, the secondarily activated sterilization solution may be additionally activated by the plasma discharge treatment. As a result, sterilizing power of the sterilization solution may be more improved.

The apparatus and method for generating an activated sterilization solution according to the embodiments of the inventive concepts may be used to maintain pure sterilization states in hospitals, laboratories, good manufacturing practice (GMP) facilities, animal breeding facilities, biological safety facilities of biological safety level (BSL)-3, and aseptic preparation and manufacture facilities of medicines and food.

According to the embodiments of the inventive concepts, the activation of the sterilization solution may be increased by the plasma, the ultraviolet light, and/or the droplet or mist generator, and thus a sterilization effect may be improved.

While the inventive concepts have been described with reference to exemplary embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. An apparatus for generating an activated sterilization solution, the apparatus comprising:
   a plasma treatment unit for performing plasma discharge treatment only on a gas, said plasma treatment unit comprising
      a gas supply line providing a flow path through which the gas flows, the supply line having a gas outlet from which the plasma-treated gas is discharged; and
      a pair of electrodes opposite to each other with the flow path interposed therebetween; and
   a sterilization solution treatment unit for changing a sterilization solution into a droplet or mist state, said sterilization solution treatment unit comprising;
      a storage container for storing the a sterilization solution; and
      a droplet or mist generator for changing the sterilization solution into the droplet or mist state,
   wherein the plasma-treated gas discharged from the gas outlet is mixed with the droplet or mist of the sterilization solution supplied from the sterilization solution treatment unit.

2. The apparatus of claim 1, wherein the droplet or mist generator comprises:
   a rotary brush; and
   a driving unit for rotating the rotary brush.

3. The apparatus of claim 2, wherein the droplet or mist generator further comprises: a blocking part fixed on a rotation path of the rotary brush over the sterilization solution and used to collide with the rotary brush.

4. The apparatus of claim 1, wherein hydrogen peroxide and a first additive are contained in the sterilization solution, and
   wherein the first additive includes at least one of sodium pyrophosphate, magnesium sulfate, sodium silicate, citric acid, or diethylenetriaminepentaacetic acid (DTPA).

5. The apparatus of claim 4, wherein hydrogen peroxide and a second additive are additionally contained in the sterilization solution, and
   wherein the second additive includes diethylenetriaminepentaacetic acid (DTPA).

6. The apparatus of claim 1, further comprising:
a sterilization solution supply unit for supplying the sterilization solution to the sterilization solution treatment unit; and
an ultraviolet irradiating unit for irradiating ultraviolet light to the sterilization solution stored in the sterilization solution supply unit.

7. The apparatus of claim 1, further comprising:
an ultraviolet irradiating unit for irradiating ultraviolet light into the sterilization solution treatment unit.

8. The apparatus of claim 1, wherein the gas includes air, and
wherein the sterilization solution in the droplet or mist state is combined with ozone included in the air treated by the plasma discharge treatment such that an activation degree of the sterilization solution in the droplet or mist state is increased.

9. The apparatus of claim 1, further comprising:
a reactor providing a space in which the gas treated by the plasma discharge treatment is mixed with the sterilization solution in the droplet or mist state.

10. A method for generating an activated sterilization solution employing the apparatus of claim 1, the method comprising:
treating a gas by plasma discharge treatment in the plasma treatment unit;
changing a sterilization solution into a droplet or mist state in the droplet or mist generator; and
mixing the gas treated by the plasma discharge treatment with the sterilization solution in the droplet or mist state.

11. The method of claim 10, wherein the gas includes air, and
wherein the sterilization solution in the droplet or mist state is combined with ozone included in the air treated by the plasma discharge treatment such that an activation degree of the sterilization solution in the droplet or mist state is increased, in the mixing of the gas treated by the plasma discharge treatment with the sterilization solution in the droplet or mist state.

12. The method of claim 10, wherein the sterilization solution includes hydrogen peroxide and an additive, and
wherein the additive includes at least one of sodium pyrophosphate, magnesium sulfate, sodium silicate, or diethylenetriaminepentaacetic acid (DTPA).

13. The method of claim 10, further comprising:
irradiating ultraviolet light to the sterilization solution,
wherein the sterilization solution is activated by the irradiating of the ultraviolet light.

14. An apparatus for generating an activated sterilization solution, the apparatus comprising:
a storage container for storing a sterilization solution;
a sterilization solution treatment unit for changing the sterilization solution into a droplet or mist state;
a circulation flow path for circulating the sterilization solution in the droplet or mist state formed in the storage container to an outside of the storage container;
a first plasma treatment unit provided on the circulation flow path and used to perform plasma discharge treatment on the sterilization solution in the droplet or mist state which circulates through the circulation flow path;
a supply flow path for supplying the sterilization solution in the droplet or mist state, which is treated by the plasma discharge treatment, from the storage container into the atmosphere; and
a valve for selectively opening or closing the circulation flow path and the supply flow path.

15. The apparatus of claim 14, further comprising:
a valve controller for controlling the valve,
wherein the valve controller controls the valve to open the supply flow path when a concentration of the sterilization solution in the droplet or mist state which is treated by the plasma discharge treatment corresponds to a predetermined reference value in the storage container.

16. The apparatus of claim 14, further comprising:
a valve controller for controlling the valve,
wherein the valve controller controls the valve to close the circulation flow path and to open the supply flow path when the sterilization solution in the droplet or mist state formed in the storage container circulates through the circulation flow path for a predetermined time.

17. The apparatus of claim 14, further comprising:
a valve controller for controlling the valve,
wherein the valve controller controls the valve to open the supply flow path when a pressure or temperature in the storage container corresponds to a predetermined reference value.

18. The apparatus of claim 14, further comprising:
an ultraviolet irradiating unit for irradiating ultraviolet light into the storage container; and
an ultraviolet irradiating unit for irradiating ultraviolet light into the sterilization solution treatment unit.

19. The apparatus of claim 14, further comprising:
a second plasma treatment unit provided on the supply flow path and used to secondarily plasma-treat the sterilization solution in the droplet or mist state which is treated by the plasma discharge treatment and is supplied into the atmosphere.

20. The apparatus of claim 1, further comprising:
a mist supply line for supplying the droplet or mist discharged from the sterilization solution treatment to the plasma-treated gas.

* * * * *